United States Patent [19]

Mueller et al.

[11] Patent Number: 4,551,279
[45] Date of Patent: Nov. 5, 1985

[54] PROTEASE INHIBITORS

[75] Inventors: Richard A. Mueller, Glencoe; Richard A. Partis, Evanston, both of Ill.

[73] Assignee: G. D. Searle & Co., Skokie, Ill.

[21] Appl. No.: 569,089

[22] Filed: Jan. 9, 1984

[51] Int. Cl.⁴ .......................................... C07C 103/46
[52] U.S. Cl. ................................. 260/404; 260/404.5
[58] Field of Search ........................ 260/404, 404.5 N

[56] References Cited

PUBLICATIONS

Nicolau et al., "N-Acylsarcosines as Inhibitors of Respiration and Glycolysis and Glycolytic Enzymes", *Biochemistry and Biophysics*, vol. 129, 1969, pp. 357–361.

Parker et al., "5-(Tetradecyloxy)-2-Furancarboxylic Acid and Related Hypolipidemic Fatty Acid-Like Alkyloxyarylcarboxylic Acids", *Journal of Medicinal Chemistry*, vol. 20, 1977, pp. 781–791.

*Primary Examiner*—Charles F. Warren
*Assistant Examiner*—Elizabeth A. Flaherty
*Attorney, Agent, or Firm*—John J. McDonnell

[57] ABSTRACT

This invention relates to methods of preventing or reducing the degradation of elastin and other proteins and thereby preventing or retarding the disease states caused by said degradation by administering compounds, some of which are novel, of the formula:

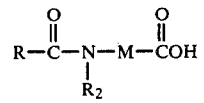

or their pharmacologically acceptable salts.

13 Claims, No Drawings

PROTEASE INHIBITORS

BACKGROUND OF THE INVENTION (a) Field of the Invention

This invention in its broadest aspect relates to protease inhibitors. In one aspect, the invention relates to certain novel methods useful in preventing or treating disease states caused by the degradative action of proteases on mammalian elastin and other proteins by administration of effective amounts of compounds of Formula I. A preferred method relates to the inhibition of the proteases elastase and cathepsin G. In other aspect, it relates to compounds of Formula I which are useful in preventing or treating disease states caused by the degradative action of proteases on mammalian elastin and other proteins.

Elastin is the functional protein component of elastic fiber tissues, a component of connective tissues. Elastic tissue is relatively rich in elastin and has a distinct rubber-like property. Most specifically, the ligamentum nuchae and the vocal cords, the vertebral ligaments flava, the aorta, and the pulmonary arteries of some mammals are considered elastic tissues. Elastic cartilaginous tissues such as those present in the ear and epiglottis are a specialized form of elastic tissue. Lung, bronchi and skin also contain elastin and are considered elastic tissue. Sandberg, et al., *New England Journal of Medicine*, Mar. 5, 1981, 566–579.

Elastase is an elastinolytic enzyme which causes degradation and fragmentation of elastic fibers by its catalytic activity against elastin. Elastases originate from a number of sources and can be found in microorganisms, snake venoms and a number of mammalian cells and tissues including pancreas, polymorphonuclear leukocytes, and macrophages. In a normally functioning mammal, elastase is required for turnover of damaged cells and the digestion of certain invading bacteria. This invention in particular relates to the class of elastases known as the Serine Proteases.

Excessive elastin degradation has been associated with pulmonary emphysema, adult respiratory-distress syndrome, arthritis, atherosclerosis, certain skin diseases, and certain inflammatory processes leading to localized protein breakdown. Werb, et al., *Journal of Investigative Dermatology*, 79:154S–159S, (1982); Rinaldo, et al., *New England Journal of Medicine*, 306:900–909, (1982). By inhibiting elastase therefore it is possible to mediate, eliminate or treat a wide variey of disease conditions.

A number of inhibitors of elastase are known. Peptide chloromethyl ketones have been shown to be irreversible inhibitors of elastase. But difficulties must be considered when the in vivo use of peptide chloromethyl ketones is contemplated. The compounds are electrophiles and can react with good nucleophiles such as the thiol groups of glutathione and various proteins. During any long term treatment with these inhibitors, such non-specific alkylation could lead to the introduction of new antigenetic determinants and an autoimmune response and/or could behave similarly to the known nitrogen mustards, etc. Peptides containing aza-amino acid residues (aza peptides) are another class of inhibitors. The effectiveness of aza-peptides as elastase inhibitors depends on the rate of acylation, which in most cases is instantaneous, and also on the rate of deacylation. As such, these compounds while useful tools in studying the in vitro properties of elastase are still largely unsuitable for in vivo use.

(b) Information Disclosure

The treatment of certain disease states by inhibitors of elastase is known as described above.

SUMMARY OF THE INVENTION

The invention relates to a method of preventing or reducing the degradation of elastin or other proteins and thereby preventing or retarding the disease states caused by said degradation by administering compounds of the formula:

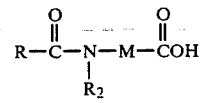

wherein R is: (a) alkyl of 15 to 19 carbon atoms, inclusive; being saturated, unsaturated or polyunsaturated;
wherein $R_2$ is:
(a) hydrogen;
(b) alkyl of 1 to 6 carbon atoms, inclusive; or
(c) Phenyl or phenyl methyl wherein the phenyl portion may optionally be substituted by Y and Z;
wherein Y and Z each being the same or different are:
(a) hydrogen;
(b) halogen;
(c) alkyl of 1 to 6 carbon atoms, inclusive;
(d) hydroxy;
(e) methoxy;
(f) acetoxy;
(g) carboxylic acid and its alkyl esters of 1 to 6 carbon atoms, inclusive;
(h) nitro; or
(i) phenyl;
wherein M is:
(a) phenyl substituted by X and W;
(b) methylene;
wherein W and X each being the same or different are:
(a) hydrogen;
(b) alkyl of from 1 to 6 carbon atoms, inclusive;
(c) hydroxy;
(d) methoxy;
(e) carboxylic acid and its alkyl esters of from 1 to 6 carbon atoms inclusive;
(f) halogen;
(g) —$NO_2$; or
(h) acetoxy;
wherein when W and X are contiguous they may be taken together to form a phenyl ring, wherein all the above compounds are unobvious and novel except wherein $R_2$ is hydrogen and with the proviso that W and X may not both be hydrogen.

Examples of alkyl of 1 to 6 carbon atoms inclusive are methyl, ethyl, propyl, butyl, pentyl, hexyl and the isomeric forms and saturated and unsaturated forms thereof.

Examples of alkoxy of 1 to 6 carbon atoms, inclusive, are methoxy, ethoxy, propoxy, butoxy, pentoxy, hexoxy and the isomeric forms thereof.

Examples of Met are $Na^+$, $K^+$, $Ca^{++}$, $Mg^{++}$, $H^+$ and $Li^+$.

Examples of alkyl of 15 to 19 carbon atoms inclusive are hexadecanoyl, 9-Z or 9-E octadecenyl, octadecanyl, 6,9,12-octadecatrienoyl,11,14-eicosadienoyl and the branched chain isomers thereof.

Examples of halogen are chloro, iodo and bromo.

Salts of the acid forms of these compounds can be prepared by neutralization with the appropriate amount of an inorganic or organic base such as sodium hydroxide, potassium hydroxide, calcium hydroxide, magnesium hydroxide, ammonia, trialkylamine, dialkylamine, monoalkylamine, dibasic amino acids, sodium acetate, potassium benzoate, triethanol amine and like bases or by direct hydrolysis of the compound wherein $R_1$ is alkyl.

The compounds useful in practicing the method of the invention are inhibitors of leucocyte elastase and cathepsin G. Since elastase is involved in the breakdown of elastin and subsequently involved in a number of disease states, a compound which blocks the action of elastase will be useful in the management, treatment and prevention of such diseases. Elastase, in addition to degrading elastin, also will hydrolyse methoxysuccinyl-ala-ala-pro-val-nitroanalide (MSN), a highly selective synthetic substance. Kakajima, K., et al., *J. Biol. Chem.*, 254, 4027 (1979). This is useful in measuring inhibition of elastase because the hydrolysis of MSN is easily quantitated by measuring the release of p-nitroaniline spectrophotometrically. Therefore, the degree of elastase inhibition can be readily measured by noting the rate of inhibition of the hydrolysis of MSN. The compounds of the invention are therefore tested in vitro as follows. The rate of hydrolysis of methoxysuccinyl-ala-ala-pro-val-nitroanalide by human leukocyte elastase is monitored spectrophotometrically in the presence and absence of test compound. The inhibition of the enzymatic reaction by 20% or more is taken as positive inhibition. $IC_{50}$ values are then determined.

The following procedure is used to test the compounds in vivo (collagen-induced rat arthritis model). The method is based on that of Trentham, D. E., Townes, A. S. and Kang, A. H. in *J. Exp. Med.* 146, 857–968 and results are evaluated thereby.

Inbred female Wistar rats (200–230 G) were randomly assigned to 3 groups of 30 animals each. Arthritis was induced by intradermal injection of bovine nasal septum Type II collagen in incomplete Freunds adjuvant.

Drug treatment was oral, once daily in 0.5 ml carboxymethyl cellulose from day 0 until sacrifice:
Group I: Test compound 50–100 mg/kg/day
Group 2: Phenylbutazone 40 mg/kg/day (positive control)
Group 3: 1% V/V carboxymethyl cellulose (negative control)

(1) Physical measurements of hind paws were made for (a) swelling across plantar region; (b) malleolar thickening; (c) extensibility of ankle joint. Results were subject to systematic statistical evaluation.

(2) Histological examination of hind paws were made in groups of 5 animals sacrificed at days 7, 14, 21 and 28. Sections were taken at 3 levels through each foot and examined for indication of disease progression.

During periods of active rheumatoid arthritis, vast numbers of human neutrophils are attracted to diseased joints where they engage in phagocytosis of locally generated immune complexes and tissue debris. During the process, enzymes (primarily elastase and cathepsin G) are released into the joint spaces. Elastase has the capacity in this situation to degrade synovial cartilage and collagen and contribute to joint destruction in a synergistic process with cathepsin G. Cathepsin G also causes conversion of angiotensin I to angiotensin II which is associated with inflammatory processes, Reilley, C. F., et al., *J. Biol. Chem.*, 257, 8619 (1982) and angiotensinogen to angiotensin II, Tonnesen, M. G., et al., *J. Clin. Invest.*, 69, 25 (1982). Natural elastase inhibitors (macro molecules such as in $\alpha_1$-proteinase inhibitor) already exist in normal serum and synovial fluid and may prevent precipitous joint destruction. Oxidation of the natural inhibitor (to the sulfoxide form) renders this material inactive. Wong, P. S. and J. Travis, *Biochem Biophys. Res. Commun.*, 96, 1449 (1980). Exogenous smaller molecular weight inhibitors of the invention can gain access to the micro-environments within the joint space not accessible to the natural inhibitors due to their molecular size, oxidation, charge repulsion or lipid solubility, and thereby inhibit or prevent further elastase-related destruction. In addition, pulmonary emphysema is a disease characterized by a progressive uninhibited proteolysis of lung tissue by enzymes such as elastase which in this case are released from leukocytes. People who are homozygotes in an $\alpha_1$-antitrypsin deficiency are predisposed to the disease. See, e.g., Turimo, et al., *Amer. J. Med.*, Vol 57, pp. 493–503 (1974). The compounds of the invention could also be used to prevent the further proteolysis of lung tissue. Again, the ability of the compounds to inhibit cathepsin G is desirable, since the combination of elastase and cathepsin G has been reported to be five times as efficient at degrading elastin as is elastase alone. Boudier, C., et al., *J. Biol. Chem.* 256, 10256 (1981). In a like manner, adult respiratory-distress syndrome, certain skin diseases, aging, and certain inflammatory processes where the disease state is connected with the localized breakdown of protein by elastase could be treated by elastase inhibitors, such as the compounds of this invention. For example, degradation of fibronectin, an important biological substance, could be inhibited. McDonald, J. A., and D. G. Kelley, *J. Biol. Chem.*, 255, 8848 (1980). The compounds may also be useful in the treatment of other enzyme related diseases, such as fribrosis related to prolylhydroxylase, hypercholesterolemia related to HMG CoA reductase, inflammatory bowel diseases and the like. The compound are in addition cytoprotective. This invention is not limited to these examples as one skilled in the art could readily apply these methods to any protease related disease or condition.

The method of the invention can be practiced in a variety of ways and the compounds can be administered in a number of dosage forms. A preferred method of delivery would be in such a manner so as to localize the action of the inhibitor. So, for example, in arthritis, the compounds could be injected directly into the affected joint, or for emphysema, the compounds could be inhaled using an aerosol or other appropriate spray. In any event, the compounds may be administered in any conventional manner. The compounds could be administerd in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory skin diseases, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for elastase inhibition by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ relatively low dosages at first, subsequently increasing the dose until a maximum response is obtained.

The compounds useful in practicing the method of this invention are prepared by methods illustrated in Chart A and B.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees celcius (°C.) and quantities of materials in grams and milliliters unless otherwise noted.

DESCRIPTION OF THE PREFERRED EMBODIMENTS

Example 1

Preparation of N-(1-oxo-9Z-octadecenyl)-N-phenylglycine, ethyl ester

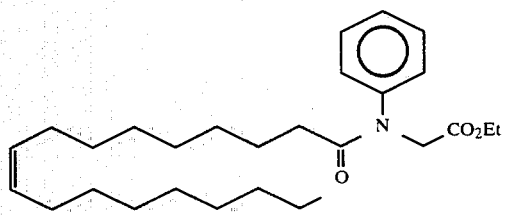

Oleoyl chloride (0.01 mole), N-phenylglycine ethyl ester (0.01 mole) and triethylamine (1.4 ml) in tetrahydrofuran (100 ml) was stirred overnight at room temperature. The solvent was removed by rotary evaporator and the residue was dissolved in ethyl acetate (50 ml) and washed with water (50 ml). The ethyl acetate solution was dried over sodium sulfate, filtered and the solvent removed by a nitrogen stream to give an oil which was purified by chromatography on silica gel to give the title compound.

Analysis calcd. for $C_{28}H_{45}NO_3$ (443.65): C, 75.80; H, 10.22; N, 3.16. C, 75.51; H, 10.32; N, 2.94.

Example 2

Preparation of N-(1-oxo-9Z-octadecenyl)-N-phenylglycine

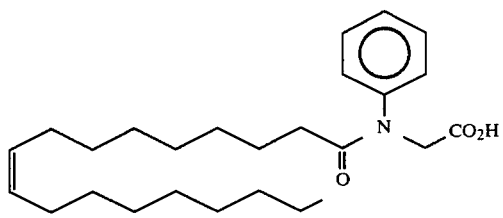

Material from Example 1 (3.0 g) and lithium hydroxide monohydrate (1.14 g) was stirred magnetically in methyl alcohol (75 ml) and water (35 ml). After two hours, water (50 ml) was added to the clear solution and the reaction was acidified with concentrated hydrochloric acid to pH 2. The methyl alcohol was removed by a rotary evaporator and replaced with ethyl acetate (100 ml). The layers were separated and the aqueous layer washed with ethyl acetate (50 ml). The combined ethyl acetate solutions were dried over sodium sulfate, filtered and the solvent removed by a rotary evaporator to give an oil. The product was purified by chromatography on silica gel to give the title compound.

Analysis calcd. for $C_{26}H_{41}NO_3$ (415.61): C, 75.14; H, 9.94; N, 3.37. Found: C, 74.94; H, 10.00; N, 3.22.

Example 3

Preparation of N-phenylglycine ethyl ester

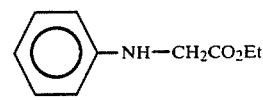

Aniline (0.096 mole), ethyl bromoacetate (0.096 mole) and sodium acetate (0.096 mole) in ethanol (150 ml) were refluxed for four hours and stirred at room temperature for 18 hours. The ethanol was removed by a rotary evaporator to give an oil. The oil was dissolved in ethyl ether (200 ml), filtered and the solvent removed by a rotary evaporator. The dark oily residue crystallized from cold hexane. Structural assignment was supported by NMR and the compound is used as is to prepare title compound of Example 1.

Example 4

Preparation of N-(4-chlorophenyl)-N-(1-oxo-9Z-octadecenyl)glycine, ethyl ester

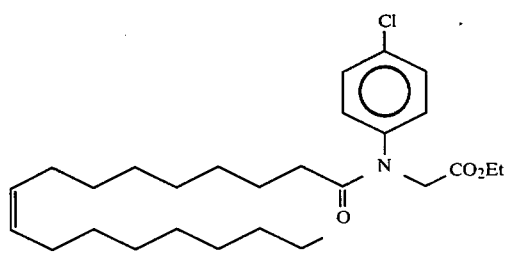

The title compound was prepared according to the method of Example 1.

Analysis calcd. for $C_{28}H_{44}ClNO_3$ (478.11): C, 70.34; H, 9.28; N, 2.93; Cl, 7.42. Found: C, 70.27; H, 9.35; N, 2.77; Cl, 7.12.

Example 5

Preparation of N-(4-chlorophenyl)-N-(1-oxo-9Z-octadecenyl)glycine

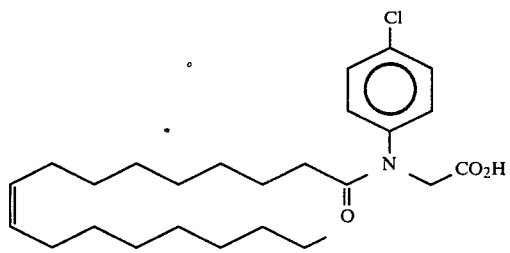

The title compound was prepared according to the method of Example 2.

Analysis calcd. for $C_{26}H_{40}ClNO_3$ (450.06): C, 69.38; H, 8.96; N, 3.11; Cl, 7.88. Found: C, 68.98; H, 8.93; N, 3.15; Cl, 7.86.

Example 6

Preparation of N-(2-hydroxyphenyl)-N-(1-oxo-9Z-octadecenyl)glycine, ethyl ester

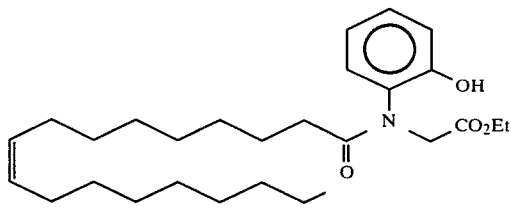

The title compound was prepared according to the method of Example 1.

Analysis calcd. for $C_{28}H_{45}NO_4$ (459.67): C, 73.16; H, 9.87; N, 3.05. Found: C, 72.86; H, 9.91; N, 2.91.

Example 7

Preparation of N-(2-hydroxyphenyl)-N-(1-oxo-9Z-octadecenyl)glycine

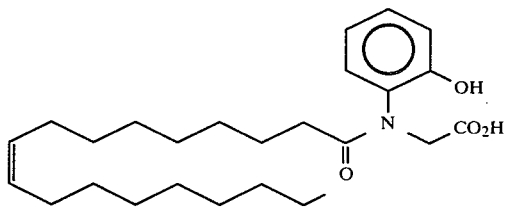

The title compound was prepared according to the method of Example 2.

Analysis calcd. for $C_{26}H_{41}NO_4$ (431.61): C, 72.35; H, 9.57; N, 3.25. Found: C, 72.31; H, 9.60; N, 3.20.

Example 8

Preparation of N-(4-hydroxyphenyl)-N-(1-oxo-9Z-octadecenyl)glycine, ethyl ester

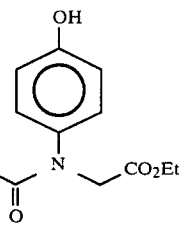

The title compound was prepared according to the method of Example 1.

Analysis calcd. for $C_{28}H_{45}NO_4$ (459.67): C, 73.16; H, 9.87; N, 3.05. Found: C, 72.84; H, 9.91; N, 2.91.

Example 9

Preparation of N-(4-hydroxyphenyl)-N-(1-oxo-9Z-octadecenyl)glycine

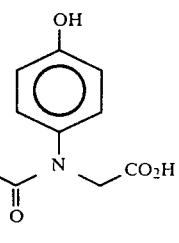

The title compound was prepared according to the method of Example 2.

Analysis calcd. for $C_{26}H_{41}NO_4$ (431.61): C, 72.35; H, 9.57; N, 3.25. Found: C, 72.39; H, 9.63; N, 3.18.

Example 10

Preparation of N-[(4-chlorophenyl)methyl]glycine, ethyl ester, hydrochloride

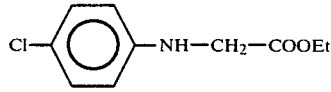

Sodium cyanoborohydride (0.10 mole) was added in one portion to a solution of glycine ethyl ester (0.10 mole) and para-chlorobenzaldehyde (0.10 mole) in methyl alcohol (125 ml) and stirred at room temperature for four days. Concentrated hydrochloric acid was added and the methyl alcohol was stripped on a rotary evaporator. After adding water (100 ml) and extracting with ethyl ether (2×75 ml) the aqueous layer was made basic with solid potassium hydroxide to pH 10, saturated with sodium chloride and the product was extracted into ethyl ether (2×100 ml). The combine extracts were dried over sodium sulfate, filtered and the solvent removed by a nitrogen stream to give an oil. The structure was confirmed by nmr and this material is used as is.

The title compound hydrochloride was prepared in the following manner. The crude material was dissolved in ethyl ether (100 ml) and with rapid stirring a saturated solution of hydrogen chloride in isopropyl alcohol was added dropwise until no further material precipitated. The material was filtered off and washed well with ethyl ether to give the title compound hydrochloride, m.p. ca. 171°-176° C.

Analysis calcd. for $C_{11}H_{15}Cl_2NO_2$ (264.15): C, 50.02; H, 5.72; N, 5.30; Cl, 26.84. Found: C, 49.68; H, 5.60; N, 5.48; Cl, 26.54.

Example 11

Preparation of N-(1-oxo-9Z-octadecenyl)-N-(phenylmethyl)glycine, ethyl ester

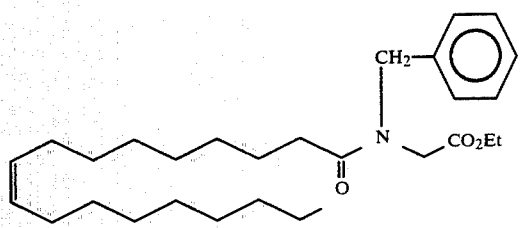

A solution of triethylamine (1.4 ml) in tetrahydrofuran (10 ml) was added dropwise to a solution of oleoyl chloride (0.01 mole) and N-benzylglycine ethyl ester (0.01 mole) in tetrahydrofuran (75 ml). Stir mixture at room temperature for 18 hours. The solvent was removed on a rotary evaporator, water (200 ml) and ethyl acetate (150 ml) added to residue, the layers separated and the aqueous layer washed with additional ethyl acetate (75 ml). The combined ethyl acetate extracts were dried over sodium sulfate, filtered and the solvent removed by rotary evaporator to give an oil. The product was purified by chromatography on silica gel to give the title compound.

Analysis calcd. for $C_{29}H_{47}NO_3$ (457.70): C, 76.10; H, 10.35; N, 3.06. Found: C, 75.74; H, 10.39; N, 2.91.

Example 12

Preparation of N-(1-oxo-9Z-octadecenyl)-N-(phenylmethyl)glycine

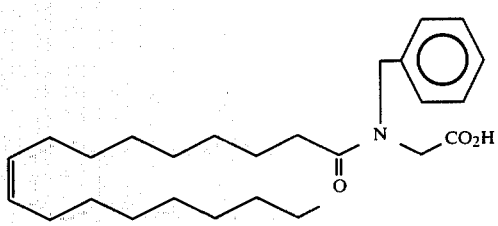

Material from Example 11 (0.0079 mole) and lithium hydroxide monohydrate (0.0315 mole) was stirred magnetically in methyl alcohol (45 ml) and water (25 ml) at 15° C. and allowed to warm to room temperature during the next 2.5 hours. The reaction was acidified to pH 2 with concentrated hydrochloric acid and the methyl alcohol was removed on a rotary evaporator, ethyl ether (50 ml) was added and the layers separated. The aqueous layer was washed with ethyl ether (50 ml). The combined ethyl ethers layers were dried over sodium sulfate, filtered and stripped of solvent on a rotary evaporator to give an oil. The product was purified by chromatography on silica gel to give the title compound.

Analysis calcd. for $C_{27}H_{43}NO_3$ (429.6): C, 75.48; H, 10.09; N, 3.26. Found: C, 75.40; H, 10.14; N, 3.12.

Example 13

Preparation of N-[(4-chlorophenyl)methyl]-N-(1-oxo-9Z-octadecenyl)glycine, ethyl ester

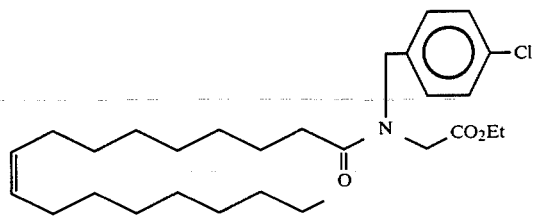

The title compound was prepared according to the method of Example 11.

Analysis calcd. for $C_{29}H_{46}NClO_3$ (492.1): C, 70.78; H, 9.42; N, 2.85; Cl, 7.20. Found: C, 70.78; H, 9.52; N, 2.68; Cl, 7.53.

Example 14

Preparation of N-[(4-chlorophenyl)methyl]-N-(1-oxo-9Z-octadecenyl)glycine

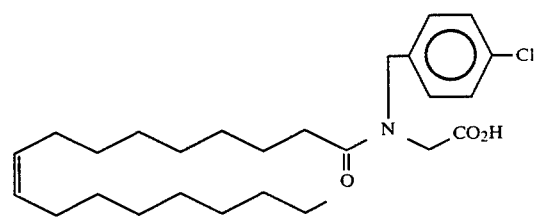

The title compound was prepared according to the method of Example 12.

Analysis calcd. for $C_{27}H_{42}ClNO_3$ (464.1): C, 69.88; H, 9.12; N, 3.02; Cl, 7.64. Found: C, 69.60; H, 9.17; N, 2.95; Cl, 7.94.

Example 15

Preparation of N-[(3,4-dichlorophenyl)methyl]-N-(1-oxo-9Z-octadecenyl)glycine, ethyl ester

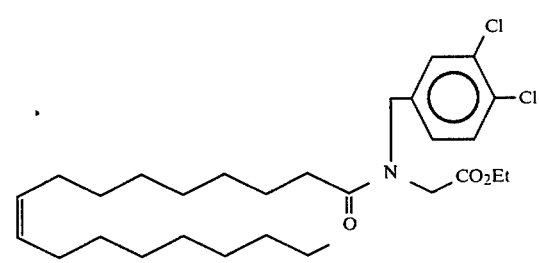

The title compound was prepared according to the method of Example 11.

Analysis calcd. for $C_{29}H_{45}Cl_2NO_3$ (526.6): C, 66.12; H, 8.61; N, 2.66; Cl, 13.46. Found: C, 66.25; H, 8.75; N, 2.57; Cl, 13.21.

Example 16

Preparation of
N-[(3,4-dichlorophenyl)methyl]-N-(1-oxo-9Z-octadecenyl)glycine

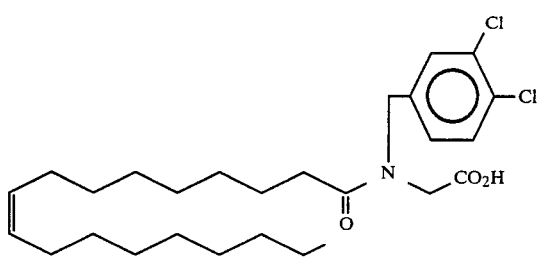

The title compound was prepared according to the method of Example 12.

Analysis calcd. for $C_{27}H_{41}NCl_2O_3$ (498.5): C, 65.05; H, 8.29; N, 2.81; Cl, 14.22. Found: C, 64.77; H, 8.29; N, 2.76; Cl, 13.97.

Example 17

Preparation of
N-([1,1'-biphenyl]-4-ylmethyl)-N-(1-oxo-9Z-octadecenyl)glycine, ethyl ester

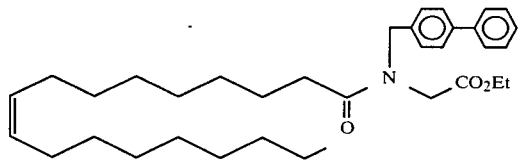

The title compound was prepared according to the method of Example 11.

This material was used after purification by chromatography on silica gel.

Example 18

Preparation of
N-([1,1'-biphenyl]-4-ylmethyl)-N-(1-oxo-9Z-octadecenyl)glycine

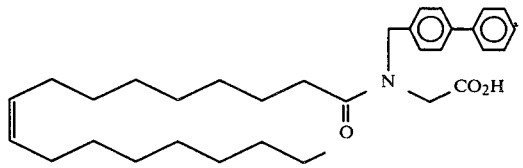

The title compound was prepared according to the method of Example 12.

Analysis calcd. for $C_{33}H_{47}NO_3$ (505.74): C, 78.37 H, 9.37; N, 2.77. Found: C, 78.12; H, 9.39; N, 2.65.

Example 19

Preparation of
N-[(2-chlorophenyl)methyl]-N-(1-oxo-9Z-octadecenyl)glycine, ethyl ester

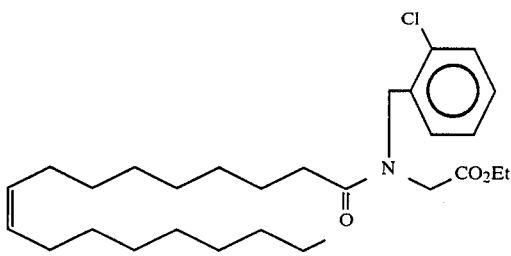

The title compound was prepared according to the method of Example 11

Analysis calcd. for $C_{29}H_{46}NO_3Cl$ (492.14): C, 70.78; H, 9.42; N, 2.85; Cl, 7.20. Found: C, 70.71; H, 9.50; N, 2.84; Cl, 7.42.

Example 20

Preparation of
N-[(2-chlorophenyl)methyl]-N-(1-oxo-9Z-octadecenyl)glycine

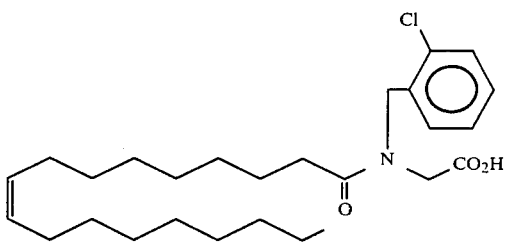

The title compound was prepared according to the method of Example 12.

Analysis calcd. for $C_{27}H_{42}ClNO_3$ (464.09): C, 69.88; H, 9.12; N, 3.02; Cl, 7.64. Found: C, 69.49; H, 9.04; N, 2.88; Cl, 7.47.

Example 21

Preparation of
N-[(4-iodophenyl)methyl]-N-(1-oxo-9Z-octadecenyl)glycine, ethyl ester

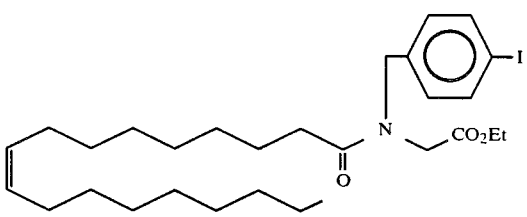

The title compound was prepared according to the method of Example 11. The material, without further purification, was used in Example 22.

Example 22

Preparation of N-[(4-iodophenyl)methyl]-N-(1-oxo-9Z-octadecenyl)glycine

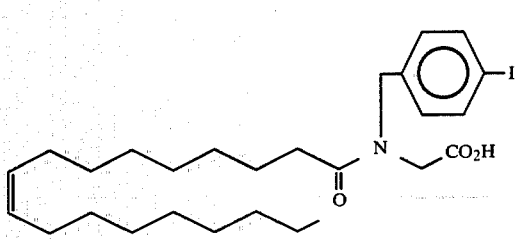

The title compound was prepared according to the method of Example 12.

Analysis calcd. for $C_{27}H_{42}NIO_3$ (555.5): C, 58.38; H, 7.62; N, 2.52. Found: C, 58.19; H, 7.53; N, 2.25.

Example 23

2-[(1-oxo-9Z-octadecenyl)amino]benzoic acid

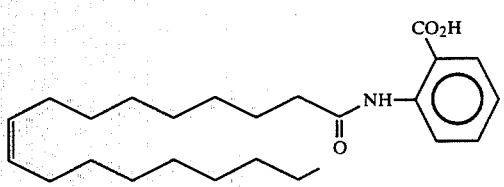

Triethylamine (20 ml) was added dropwise with stirring to a mixture of oleoyl chloride (0.02 mole) and anthranilic acid (0.02 mole) in methylene chloride (150 ml) over 15 minutes. After stirring at room temperature for 18 hours the solvent and triethylamine was removed on a rotary evaporator. Toluene (150 ml) was added and the process repeated. Ethyl acetate (100 ml) was added to the residue and after stirring for a short period was filtered and stripped of solvent on a rotary evaporator. The residue was purified by chromatography on silica gel to give the title compound, m.p. ca. 43°–51° C.

Analysis calcd. for $C_{25}H_{39}NO_3$ (401.6): C, 74.77; H, 9.79; N, 3.49. Found: C, 74.86; H, 10.20; N, 3.62.

Example 24

Preparation of 4-[(1-oxo-9Z-octadecenyl)amino]benzoic acid

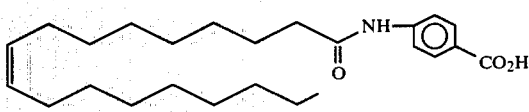

The title compound was prepared according to the method of Example 23.

m.p. ca. 168°–172° C.

Analysis calcd. for $C_{25}H_{39}NO_3$ (401.6): C, 74.77; H, 9.79; N, 3.49. Found: C, 75.04; H, 9.71; N, 3.48.

Example 25

Preparation of 3-[(1-oxo-9Z-octadecenyl)amino]benzoic acid

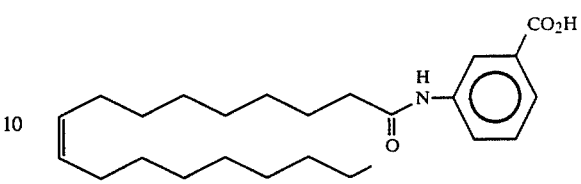

The title compound was prepared according to the method of Example 23.

m.p. ca. 201°–207° C.

Analysis calcd. for $C_{25}H_{39}NO_3$ (401.6): C, 74.77; H, 9.79; N, 3.49. Found: C, 74.67; H, 9.62; N, 3.44.

Example 26

Preparation of 3-[(1-oxo-9Z-octadecenyl)amino]-2-naphthalenecarboxylic acid

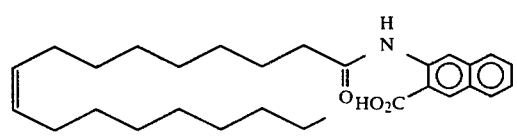

The title compound was prepared according to the method of Example 23.

Analysis calcd. for $C_{29}H_{41}NO_3$ (451.65): C, 77.12; H, 9.15; N, 3.10. Found: C, 76.84; H, 9.25; N, 2.96.

Example 27

Preparation of 2-amino-3-methylbenzoic acid

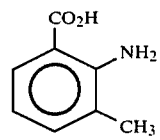

A solution of 3-methyl-2-nitrobenzoic acid (7 g) in ethanol (250 ml) was reduced with hydrogen gas at 2 psi over 5% palladium/carbon (0.7 g) catalyst. After hydrogen uptake ceased, the mixture was filtered and solvent removed by a rotary evaporator to give a white solid. Purification was by recrystallization from ethyl ether-hexane, m.p. ca. 170°–173° C.

Analysis calcd. for $C_8H_9NO_2$ (151.2): C, 63.57; H, 6.00; N, 9.27. Found: C, 63.19; H, 6.00; N, 9.16.

Example 28

Preparation of 3-methyl-2-[(1-oxo-9Z-octadecenyl)amino]benzoic acid

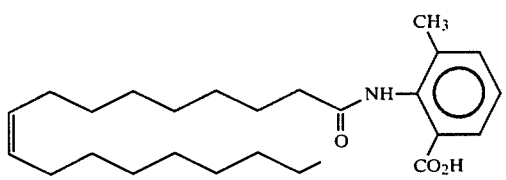

The title compound was prepared from the reaction of oleoyl chloride and material from Example 27 according to the method of Example 23, m.p. ca. 78°–80° C.

Analysis calcd. for $C_{26}H_{41}NO_3$ (415.61): C, 75.14; H, 9.94; N, 3.37. Found: C, 75.20; H, 9.93; N, 3.61.

Example 29

Preparation of 3-methoxy-2-[(1-oxo-9Z-octadecenyl)amino]benzoic acid

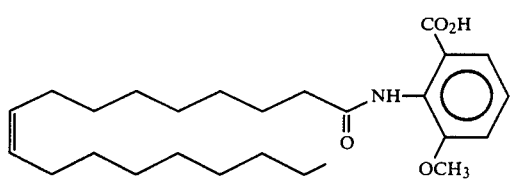

The title compound was prepared according to the method of Example 28.

Analysis calcd. for $C_{26}H_{41}NO_4$ (431.6): C, 72.35; H, 9.58; N, 3.25. Found: C, 72.68; H, 9.61; N, 3.21.

Example 30

Preparation of 2-methyl-6-[(1-oxo-9Z-octadecenyl)amino]benzoic acid

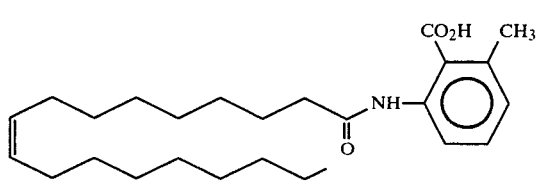

The title compound was prepared according to the method of Example 28.

Analysis calcd. for $C_{26}H_{41}NO_3$ (415.61): C, 75.14; H, 9.94; N, 3.37. Found: C, 74.91; H, 10.00; N, 3.04.

Example 31

Preparation of 2-(N-methyl)aminobenzoic acid

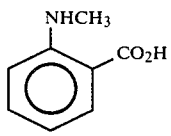

A solution of 2-aminobenzoic acid (25 g) in ethanol (300 ml) reacted with an excess of paraformaldehyde and then reduced with hydrogen gas at 60 psi over platinum oxide (25 g) catalyst. After hydrogen uptake ceased, the mixture was filtered and the solvent removed on a rotary evaporator. The product was purified by chromatography on silica gel and the structure confirmed by nmr and infrared analysis.

Example 32

Preparation of 2-[methyl(1-oxo-9-Z-octadecenyl)amino]benzoic acid

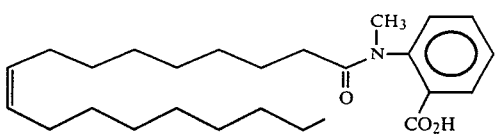

The title compound was prepared from the reaction of oleoyl chloride and material from Example 31 according to the method of Example 23.

Analysis calcd. for $C_{26}H_{41}NO_3$ (415.60): C, 75.14; H, 9.94; N, 3.37. Found: C, 74.75; H, 9.98; N, 3.25.

Example 33

Preparation of 5-[(1-oxo-9Z-octadecenyl)amino]-1,3-benzenedicarboxylic acid

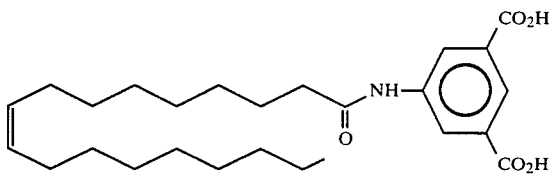

Triethylamine (20 ml) was added dropwise to a solution of 5-aminoisophthalic acid (0.02 mole) and oleoyl chloride (0.02 mole) in methylene chloride (150 ml) and the cloudy solution stirred at room temperature for 18 hours. The solvent was removed under a nitrogen stream. Hydrochloric acid (1 N.; 200 ml) was added to the residue with stirring. The hydrochloric acid was decanted and the residue treated with hot ethyl acetate (150 ml). After filtering off insoluble material, the solvent was removed by a rotary evaporator. The title compound was purified by chromatography on silica gel m.p. ca. 265° C.

Analysis calcd. for $C_{26}H_{39}NO_5$ (445.6): C, 70.08; H, 8.82; N, 3.14. Found: C, 69.94; H, 8.85; N, 2.83.

Example 34

Preparation of 2-[(1-oxo-9Z-octadecenyl)amino]-1,3-benzenedicarboxylic acid

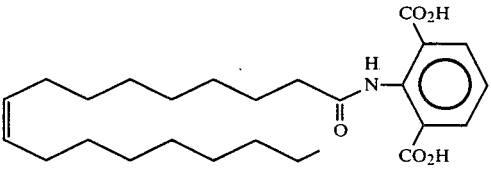

The title compound was prepared according to the method of Example 33. m.p. ca. 142°–146° C.

Analysis calcd. for $C_{26}H_{39}NO_5$ (445.6): C, 70.08; H, 8.82; N, 3.14. Found: C, 70.19; H, 8.93; N, 3.14.

Example 35

Preparation of 2-amino-1,3-benzenedicarboxylic acid

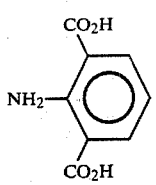

The title compound was prepared according to the method of Example 27 with tetrahydrofuran used as a solvent.

Analysis calcd. for $C_8H_7NO_4$ (181.15): C, 53.04; H, 3.89; N, 7.73. Found: C, 52.92; H, 4.01; N, 7.49.

Example 36

Preparation of 2-[(1-oxo-9Z-octadecenyl)amino]-1,4-benzenedicarboxylic acid

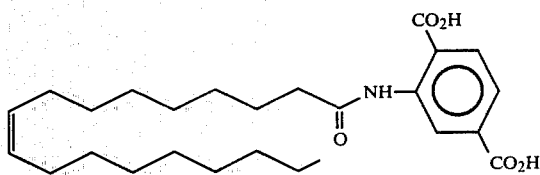

The title compound was prepared according to the method of Example 33. m.p. ca. 237°–240° C.

Analysis calcd. for $C_{26}H_{39}NO_5$ (445.6): C, 70.08; H, 8.82; N, 3.14. Found: C, 69.82; H, 8.78; N, 3.09.

Example 37

Preparation of dimethyl 5-[(1-oxo-9Z-octadecenyl)amino]-1,3-benzenedicarboxylate

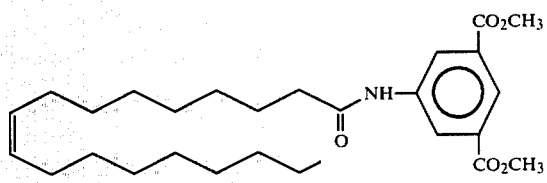

A solution of thionyl chloride (0.2 ml) in methylene chloride (5 ml) was added dropwise to a solution of the product from example 33 ($1.1 \times 10^{-3}$ mole) in methanol (25 ml) over 3 minutes and stirred at room temperature for 18 hours. After warming on the steambath for 1.5 hours, water (25 ml) was added and the product was extracted into ethyl acetate (2×25 ml). The combined ethyl acetate extracts were dried over sodium sulfate, filtered and stripped to give an oil. The product was purified by chromatography on silica gel to give the title compound, m.p. ca. 55°–59° C.

Analysis calcd. for $C_{28}H_{43}NO_5$ (473.65): C, 71.00; H, 9.15; N, 2.96. Found: C, 70.88; H, 9.32; N, 2.85.

Example 38

Preparation of 3-amino-5-carboxymethylbenzoic acid

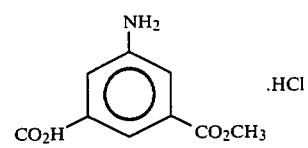

One equivalent of lithium hydroxide monohydrate was added to a solution of dimethyl-5-aminoisophthalate (prepared from 5-aminoisophthalic acid, thionyl chloride and methanol) in methanol (75 ml) and water (20 ml) and stirred at room temperature for 24 hours. The cloudy solution was heated for 2 hours on a hot plate and stripped of methanol on a rotary evaporator. The residue was triturated with hydrochloric acid and then extracted into methylene chloride (2×75 ml). The combined methylene chloride extracts were dried over sodium sulfate, filtered and stripped of solvent. The material was purified by crystallization from methanol-ethyl ether. m.p. 214°–220° C.

Analysis calcd. for $C_9H_{10}NO_4Cl$ (231.6): C, 46.67; H, 4.35; N. 6.04. Found: C, 46.16; H, 4.41; N, 5.91.

Example 39

Preparation of 5-[(1-oxo-9Z-octadecenyl)amino]-1,3-benzene dicarboxylic acid, 1-methyl ester

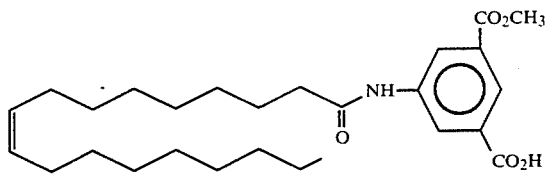

The title compound was prepared according to the method of example 33 using the material prepared in example 38. m.p. 133°–138° C.

Analysis calcd. for $C_{27}H_{41}NO_5$ (459.62): C, 70.56; H, 8.99; N, 3.05. Found: C, 70.41; H, 9.09; N, 3.36.

Example 40

Preparation of 2-methoxy-5-nitrobenzoic acid

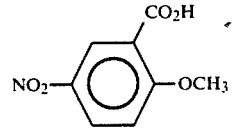

A mixture of 5-nitrosalicylic acid (0.10 mole) and potassium carbonate (0.22 mole) in m-xylene (200 ml) was refluxed for 3 hours. After cooling the mixture, methyl-p-toluene sulfonate (0.30 mole) was added dropwise over 10 minutes and again brought to reflux (18 hours) where the water formed was removed by a Dean-Stark trap. The mixture was filtered hot and the solid was washed with hot toluene. The filtrate was stripped by rotary evaporator to give methyl 2-methoxy-5-nitro benzoate, a solid, (structure confirmed by NMR).

This material was hydrolyzed to the title compound with sodium carbonate in a mixture of hot methanol and water. After workup in the usual manner the title compound was isolated as a solid. (m.p. 161°-162° C.)

Analysis calcd. for $C_8H_7NO_5$ (197.15): C, 48.74; H, 3.58; N, 7.10. Found: C, 48.56; H, 3.63; N, 7.02.

Example 41

Preparation of 5-amino-2-methoxybenzoic acid

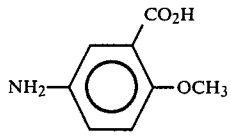

The title compound was prepared according to the method of example 27, m.p. ca. 163°-166° C. The structure was confirmed by NMR and IR.

Example 42

Preparation of 2-methoxy-5-[(1-oxo-9Z-octadecenyl)amino]benzoic acid

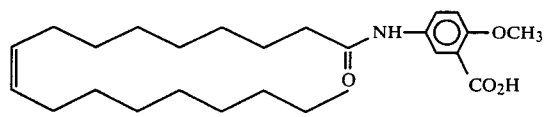

The title compound was prepared according to the method of example 23, m.p. ca. 128°-131° C.

Analysis calcd. for $C_{26}H_{41}NO_4$ (431.6): C, 72.35; H, 9.58; N, 3.25. Found: C, 72.33; H, 9.58; N, 3.16.

Example 43

Preparation of 2-acetyloxy-5-nitrobenzoic acid

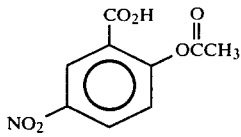

A mixture of 5-nitrosalicyclic acid (5 g), acetic anhydride (13 ml) and sulfuric acid (0.3 ml) was heated at 55° C. for 10 minutes. After the solution was removed from the hot water bath and stirred at room temperature for 1 hour it was poured into water (200 ml). The mixture was stirred for 10 minutes and filtered. The solid was stirred with water (100 ml), filtered by suction and air dried to give the title compound, m.p. ca, 165°-168° C.

Analysis calcd. for $C_9H_7NO_6$ (225.16): C, 48.01; H, 3.13; N, 6.22. Found: C, 47.79; H, 3.16; N, 6.15.

Example 44

Preparation of 5-amino-2-acetyloxybenzoic acid

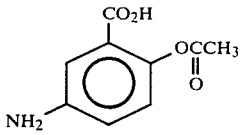

The title compound was prepared according to the method of example 27, m.p. ca. 202°-206° C.

Analysis calcd. for $C_9H_9NO_4$ (195.17): C, 55.39; H, 4.65; N, 7.18. Found: C, 55.60; H, 4.84; N, 7.05.

Example 45

Preparation of 2-(acetyloxy)-5-[(1-oxo-9Z-octadecenyl)amino]benzoic acid

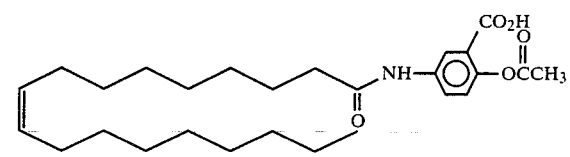

The title compound was prepared according to the method of example 23, m.p. ca. 140°-145° C.

Analysis calcd. for $C_{26}H_{39}NO_5$ (445.6): C, 70.08; H, 8.82; N, 3.14. Found: C, 70.19; H, 8.93; N, 3.14.

Example 46

Preparation of methyl 2-hydroxy-5-[(1-oxo-9Z-octadecenyl)amino]benzoate

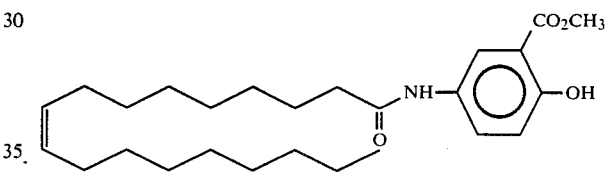

The title compound was prepared according to the method of example 23, m.p. ca. 67°-72° C. (The starting material, methyl-5-amino-2-hydroxy benzoate, was prepared from 5-amino-salicyclic acid, thionyl chloride and methanol in the usual manner (Example 45).

Analysis calcd. for $C_{26}H_{41}NO_4$ (431.61): C, 72.35; H, 9.57; N, 3.25. Found: C, 72.37; H, 9.58; N, 3.22.

Example 47

Preparation of methyl 5-amino-2-methoxybenzoate hydrochloride

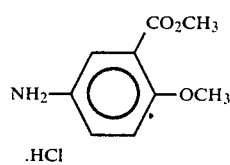

The title compound was prepared by reaction of Example 41, thionyl chloride and methanol. The title compound was purified by recrystallization from methanol-ethyl ether.

Analysis calcd. for $C_9H_{12}NO_3Cl$ (217.65): C, 49.67; H, 5.56; N, 6.44; Cl, 16.29. Found: C, 49.34; H, 5.52; N, 6.26; Cl, 16.07.

Example 48

Preparation of methyl 5-[(1-oxo-9Z-octadecenyl)amino]methoxybenzoate

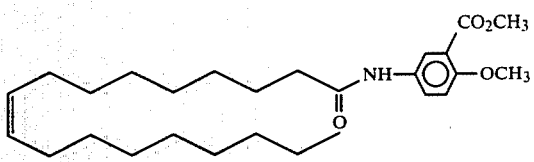

The title compound was prepared according to the method of example 23, m.p. ca. 74°–78° C.

Analysis calcd. for $C_{27}H_{43}NO_4$ (445.6): C, 72.77; H, 9.72; N, 3.14. Found: C, 72.57; H, 9.83; N, 3.25.

Example 49

Preparation of methyl 2-acetyloxy-5-nitrobenzoate

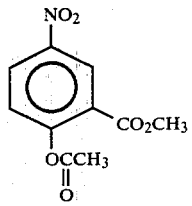

Thionyl chloride (30 ml) was added dropwise to a solution of 5-nitro salicyclic acid (25 g) in methanol (300 ml) over 30 minutes. After stirring at room temperature for 18 hours the solvent and excess thionyl chloride was removed on a rotary evaporator. The residue was dissolved in hot toluene, filtered and cooled. A white solid methyl-2-hydroxy-5-nitro-benzoate was isolated by filtration. This material was treated with acetic anhydride (20 ml) and sulfuric acid (8 drops) at 50° C. for 1 hour. The reaction was cooled, poured into cold water (250 ml), stirred for 30 minutes and the title compound was isolated by vacuum filtration. This material was washed well with water, m.p. ca. 70°–72° C.

Analysis calcd. for $C_{10}H_9NO_6$ (239.2): C, 50.22; H, 3.79; N, 5.86. Found: C, 50.26; H, 3.67; N, 5.83.

Example 50

Preparation of methyl 2-acetyloxy-5-[N-methylamino]benzoate

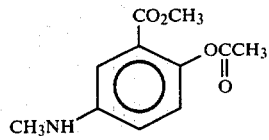

The title compound was prepared according to the method of example 31. The structure was confirmed by NMR and IR.

Example 51

Preparation of methyl 2-(acetyloxy)-5-[N-methyl(1-oxo-9Z-octadecenyl)amino]benzoate

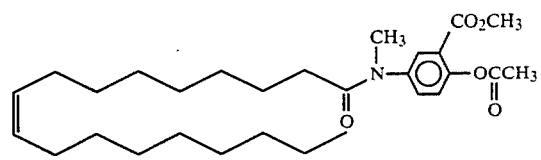

The title compound was prepared according to the method of example 23.

Analysis calcd. for $C_{29}H_{15}NO_5$ (487.68): C, 71.42; H, 9.30; N, 2.87. Found: C, 71.36; H, 9.65; N, 2.84.

Example 52

Preparation of 2-(acetyloxy)-5-[N-methyl(1-oxo-9Z-octadecenyl)amino]benzoic acid

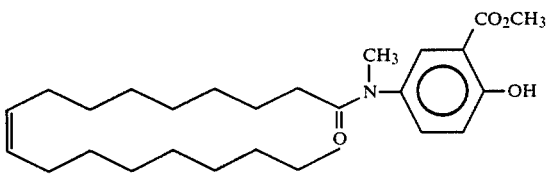

Treatment of the product of Example 51 with lithium hydroxide monohydrate in methanol-water and work-up in the usual manner gave the title compound. The structure was confirmed by NMR spectroscopy.

Example 53

Preparation of 2-hydroxy-5-[methyl(1-oxo-9Z-octadecenyl)amino]-benzoic acid

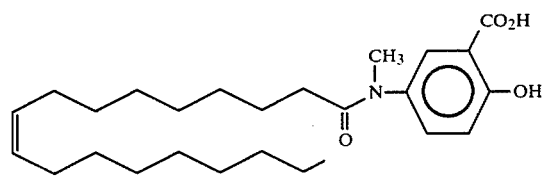

Treatment of the product of Example 52 with sodium hydroxide in hot methanol-water and work-up in the usual manner gas the title product. Purification was by chromatography on silica gel.

Analysis calcd. for $C_{26}H_{41}NO_4$ (431.61): C, 72.35; H, 9.57; N, 3.25. Found: C, 72.23; H, 9.72; N, 3.17.

Example 54

Preparation of 2-hydroxy-4-[(1-oxo-9Z-octadecenyl)amino]benzoic acid

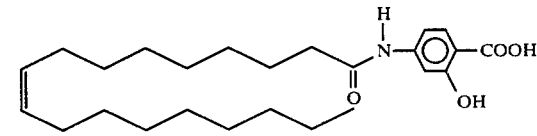

3.0 g of oleoyl chloride was added to 1.58 g of 4-aminosalicylic acid at room temperature in tetrahydrofuran solvent. 1.4 ml of triethylamine was then added and the mixture stirred at room temperature for about 24 hours. Chromatography on silica gel gave 0.812 g of product which could be further purified by recrystallization from ethyl acetate with added cyclohexane—m.p. ca. 168°–172° C.

Example 55

2-hydroxy-5-[(1-oxo-9Z-octadecenyl)amino]benzoic acid

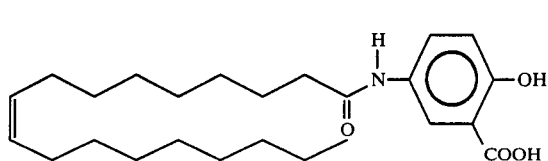

3.0 g of oleoyl chloride; 1.58 g of 5-aminosalyclic acid and 1.4 ml of triethylamine were treated in Example 51 to give the title compound m.p. ca. 179°–183° C.

Example 56

Preparation of 2-hydroxy-5-[(1-oxo-9Z-octadecanyl)amino]benzoic acid

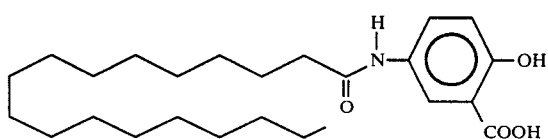

0.5 g of the product from Example 55 was treated with hydrogen and palladium on carbon in solvent. The solvent was removed under a stream of nitrogen. The residue was recrystallized from ethyl acetate to give title compound—m.p. ca. 196°–200° C.

Example 57

Preparation of 3-hydroxy-4-methyl-2-[(1-oxo-9Z-octadecenyl)amino]-benzoic acid

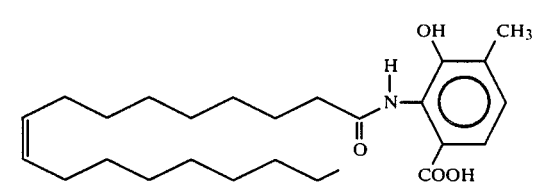

2.4 g of 2-amino-3-hydroxy-4-methylbenzoic acid was suspended in about 50 ml of tetrahydrofuran then 4.5 g of oleoyl chloride was added and the mixture stirred for two hours at room temperature. 2.1 ml of triethylamine was added followed 2 hours later by an additional 2.1 ml. The mixture was stirred at room temperature for about 62 hours then refluxed for about 18 hours. The mixture was cooled to room temperature and added, with stirring, to about 600 ml of water, extracted with cyclohexane, the organic extracts combined, dried over sodium sulfate and the solvent removed to give an oil. The oil was crystallized from pentane to give the desired title compound—m.p. ca. 82°–86° C.

Example 58

Preparation of 3-hydroxy-4-[(1-oxo-9Z-octadecenyl)amino]benzoic acid

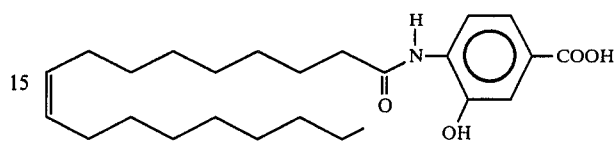

In the manner of Example 57, 3.06 g of 3-hydroxy-4-amino-benzoic acid, 6.0 g of oleoyl chloride and 5.6 ml of triethylamine were reacted. The crystals obtained upon addition of the reaction mixture to water were recrystallized from ethyl acetate to give the title compound—m.p. ca. 222°–226° C.

Example 59

2-chloro-5-[(1-oxo-9Z-octadecenyl)amino]benzoic acid

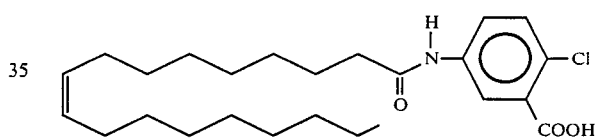

In the manner of Example 57 were reacted 3.47 g of 2-chloro-5-amino benzoic acid, 6.0 g of oleoyl chloride and 5.6 ml of triethylamine. The material obtained upon addition of the reaction mixture to water was crystallized from ethyl acetate/cyclohexane to yield the title compound—m.p. ca. 91°–97° C.

Example 60

Preparation of 4-nitro-2-[(1-oxo-9Z-octadecenyl)amino]benzoic acid

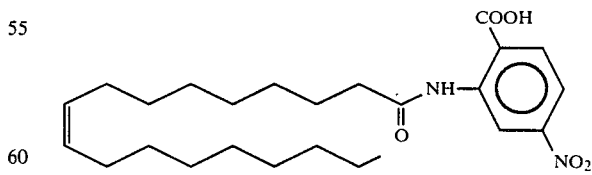

In the manner of Example 57 were reacted 2.7 g of 2-amino-4-nitrobenzoic acid, 4.5 g of oleoyl chloride and 4.2 ml of triethylamine. Recrystallization of the solid obtained from ethyl acetate gave the title compound—m.p. ca. 135°–140° C.

Example 61

Preparation of 4-hydroxy-3-[(1-oxo-9Z-octadecenyl)amino]benzoic acid

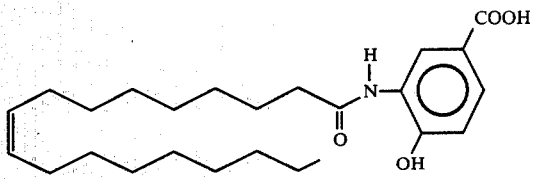

In the manner of Example 57 were reacted 4.0 g of 3-amino-4-hydroxybenzoic acid, 4.5 g of oleoyl chloride and 4.2 ml of triethylamine. Recrystallization from ethyl acetate gave the title compound—m.p. ca. 241°–245° C.

Example 62

Preparation of 2-hydroxy-5-[(1-oxododecyl)amino]benzoic acid

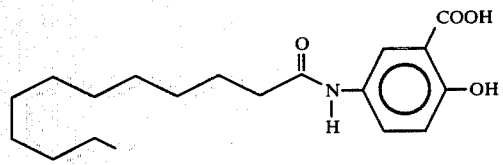

In the manner of Example 57 were reacted 4.38 g of lauryl chloride, 3.0 g of 5-amino-salicylic acid and 2.8 ml of triethylamine. Recrystallization from methanol/ethyl acetate then methanol gave the title compound—m.p. ca. 201°–205° C.

Example 63

Preparation of 2-hydroxy-5-[(1-oxooctyl)amino]benzoic acid

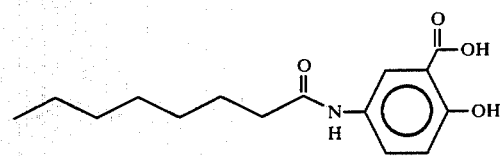

In the manner of Example 57 were reacted 3.4 ml of octanoyl chloride, 3.0 g of 5-amino salicylic acid and 2.8 ml of triethylamine. Recrystallization from methanol gave the title compound—m.p. ca. 200°–204° C.

Example 64

Preparation of 3-hydroxy-2-[(1-oxo-9Z-octadecenyl)amino]benzoic acid

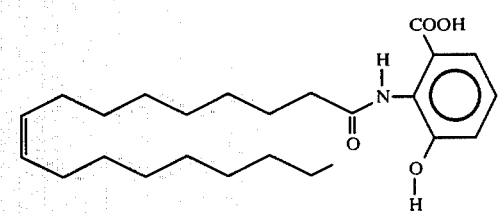

In the manner of Example 57 were reacted 3.8 g of 2-amino-3-hydroxybenzoic acid, 7.4 g of oleoyl chloride and 7.0 ml of triethylamine. Recrystallization from ethyl acetate cyclohexane gave the title compound.

Analysis calcd. for $C_{24}H_{39}NO_4$ (417.59): C, 71.91; H, 9.41; N, 3.35. Found: C, 72.04; H, 9.48; N, 3.40.

Example 65

Preparation of 2-hydroxy-5-[(1-oxo-9E-octadecenyl)amino]benzoic acid

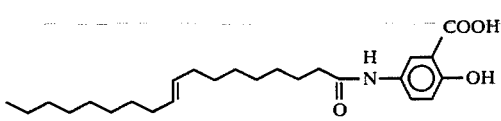

In the general manner of Example 57 were reacted 0.7 g of 5-aminosalicylic acid, 1.39 g of elaidoyl chloride and 1.4 ml of triethylamine. The material obtained was recrystallized from methanol containing charcoal to give the title compound—m.p. ca. 180°–184.5° C.

Example 66

Preparation of methyl 2-methyloleoate.

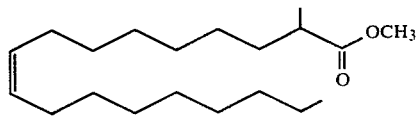

A solution of methyl oleate (0.054 mole) in tetrahydrofuran (100 ml) was added dropwise to a freshly prepared cold solution of lithium isopropyl cyclohexyl amide (1.2 eq.) in tetrahydrofuran (400 ml) over 4.75 hrs. Methyl iodide (1.5 eq.) was added dropwise rapidly and the reaction was allowed to come to room temperature. The reaction was stripped of solvent to give an orange oil. The material was added to 1N hydrochloric acid (100 ml) and extracted into ethyl ether. The ethyl ether was washed with water (100 ml), dried over sodium sulfate, filtered and stripped to an oil which was identified as the title compound by spectral analysis and used in Example 67.

Example 67

Preparation of methyl-2,2-dimethyloleate

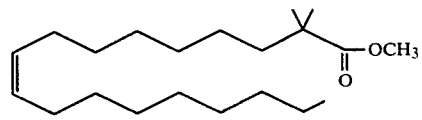

The material of Example 66 (16 g) was treated in the same manner as Example 66 to give the title compound. Its identity was confirmed by NMR, CMR, and IR spectra. This material (98% by G.L.C. analysis) was used without further purification in Example 68.

Example 68

Preparation of 2,2-dimethyloleoic acid

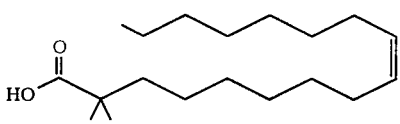

The material from Example 67 was treated with methyl alcohol (300 ml), lithium hydroxide monohydrate (6.3 g) and water (100 ml) and stirred for about 18 hrs. at room temperature. After warming on a hot plate for 6 hrs. and allowing to stir ovrnight at room temperature, the methyl alcohol was removed on a rotary evaporator and the aqueous residue acidified with 1N hydrochloric acid to pH 2. The product was extracted into ethyl acetate (2×100 ml), dried over sodium sulfate, filtered and stripped of solvent to yield an oil. The title compound was purified by chromatography on silica gel.

Analysis calcd. for $C_{20}H_{38}O_2$ (310.52): C, 77.36; H, 12.33. Found: C, 77.60; H, 12.48.

Example 69

Preparation of 2-hydroxy-5-[(1-oxo-2,2-dimethyl-9Z-octadecenyl)amino]benzoic acid

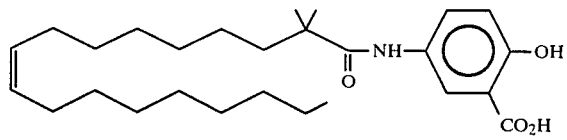

The material from Example 68 (0.007 mole) in cold benzene (40 ml) was treated with oxalyl chloride (0.007 mole). After stirring at room temperature for about 4.5 hrs. the solvent was removed on a rotary evaporator. The acid chloride was treated with 5-aminosalicylic acid in the manner of Example 23.

Analysis calcd. for $C_{27}H_{43}NO_4$ (445.62): C, 72.76; H, 9.73; N, 3.14. Found: C, 72.45; H, 9.81; N, 2.95.

CHART A

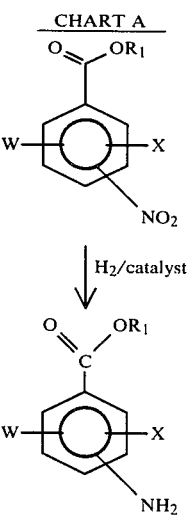

-continued
CHART A

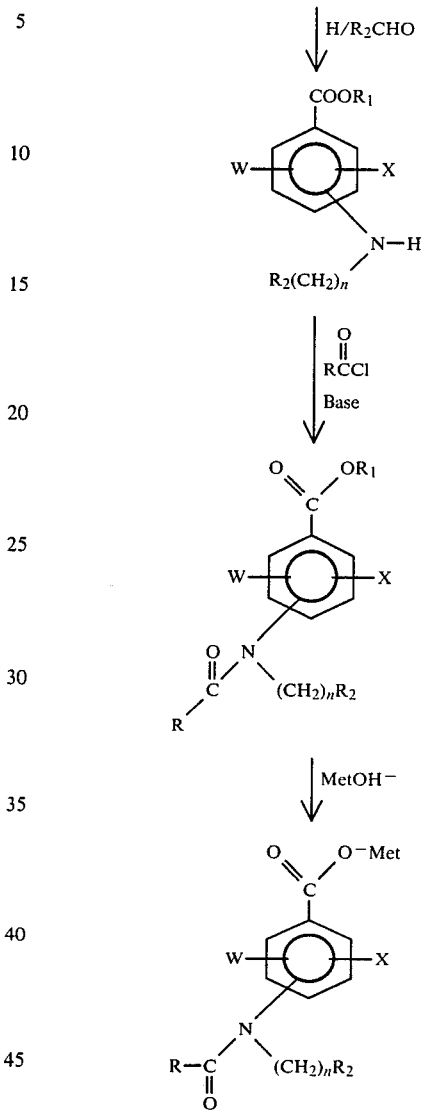

$n = 0,1$
$R_1 = H$ or alkyl

CHART B

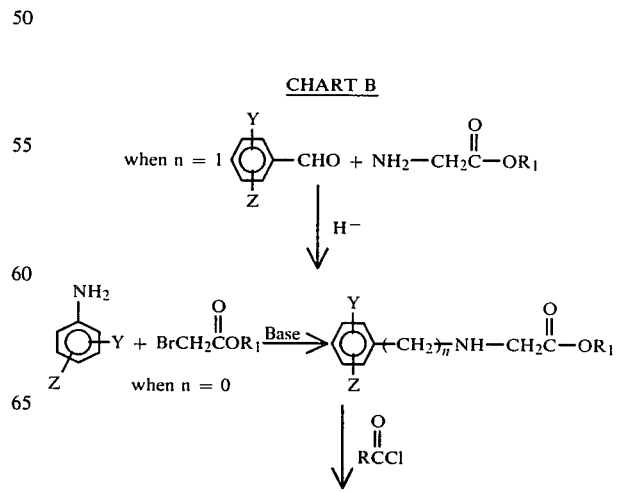

-continued
CHART B

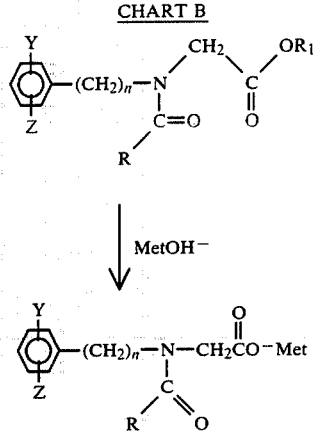

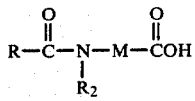

n = 0,1  R₁ = H or alkyl

What is claimed is:
1. Compounds of the formula:

$$R-\overset{O}{\underset{}{C}}-\underset{R_2}{N}-M-\overset{O}{\underset{}{C}}OH$$

wherein R is:
(a) alkyl of 15 to 19 carbon atoms, inclusive; being saturated, unsaturated or polyunsaturated;
wherein $R_2$ is: phenyl or phenyl methyl wherein the phenyl portion may optionally be substituted by Y and Z;
wherein Y and Z each being the same or different are:
(a) hydrogen;
(b) halogen;
(c) alkyl of 1 to 6 carbon atoms, inclusive;
(d) hydroxy;
(e) methoxy;
(f) acetoxy,
(g) carboxylic acid and its alkyl esters of 1 to 6 carbon atoms, inclusive;
(h) nitro; or
(i) phenyl;
wherein M is:
(a) phenyl substituted by X and W;
(b) methylene;
wherein W and X each being the same or different are:
(a) hydrogen;
(b) alkyl of from 1 to 6 carbon atoms, inclusive;
(c) hydroxy;
(d) methoxy;
(e) carboxylic acid and its alkyl esters of from 1 to 6 carbon atoms inclusive;
(f) halogen;
(g) —NO₂; or
(h) acetoxy;
wherein when W and X are contiguous they may be taken together to form a phenyl ring; and
wherein W and X may not both be hydrogen.
2. A compound according to claim 1 wherein $R_2$ is phenyl.
3. N-(4-chlorophenyl)-N-(1-oxo-9Z-octadecenyl)glycine a compound according to claim 2.
4. N-(4-hydroxyphenyl)-N-(1-oxo-9Z-octadecenyl)glycine a compound according to claim 2.
5. N-(1-oxo-9Z-octadecenyl)-N-phenylglycine a compound according to claim 2.
6. N-(2-hydroxyphenyl)-N-(1-oxo-9Z-octadecenyl)glycine a compound according to claim 2.
7. A compound according to claim 1 wherein $R_2$ is alkyl phenyl.
8. N-(1-oxo-9Z-octadecenyl)-N-(phenylmethyl)glycine a compound according to claim 7.
9. N-[(3,4-dichlorophenyl)methyl]-N-(1-oxo-9Z-octadecenyl)glycine a compound according to claim 7.
10. N-[(2-chlorophenyl)methyl]-N-(1-oxo-9Z-octadecenyl)glycine a compound according to claim 7.
11. N-([1,1'-biphenyl]-4-ylmethyl)-N-(1-oxo-9Z-octadecenyl)glycine a compound according to claim 7.
12. N-[(4-iodophenyl)methyl]-N-(1-oxo-9Z-octadecenyl)glycine a compound according to claim 7.
13. N-[(4-chlorophenyl)methyl]-N-(1-oxo-9Z-octadecenyl)glycine a compound according to claim 7.

* * * * *